United States Patent [19]

DiTuro

[11] Patent Number: 5,275,943
[45] Date of Patent: Jan. 4, 1994

[54] TIMED-RELEASE TABLETS FOR BIOLOGICAL DEGRADATION OF ORGANIC MATTER

[76] Inventor: John W. DiTuro, 30 Stockton Lake Blvd., Manasquan, N.J. 08736

[21] Appl. No.: 684,191

[22] Filed: Apr. 12, 1991

[51] Int. Cl.$^5$ .................. C12N 11/12; C12N 11/04; C02F 3/00
[52] U.S. Cl. .................... 435/179; 210/601; 435/182; 435/262.5; 435/821
[58] Field of Search ............... 435/174, 177, 179, 182, 435/262.5, 821; 424/400; 210/601, 605, 606, 620, 627

[56] References Cited

U.S. PATENT DOCUMENTS 3,242,055  3/1966  De Lucia ........................... 435/176
5,106,633  4/1992  Edens et al. ..................... 435/182 X

FOREIGN PATENT DOCUMENTS 0320483  6/1989  European Pat. Off. ............ 435/182
58-189031 11/1983  Japan ................................ 435/182

Primary Examiner—David M. Naff
Attorney, Agent, or Firm—Isaac Angres

[57] ABSTRACT

Tablets are formed that release components over time for biological degradation of organic matter such as sewage sludge, petroleum hydrocarbons, pesticides and herbicides. The tablets contain an inner-core of a dormant live microorganism, an inner-coating over the inner-core of water soluble hydroxypropyl methylcellulose or polyethylene glycol, an outer-layer over the inner-coating of sodium sulfate coated sodium carbonate peroxyhydrate particles, and an outer-coating over the outer-layer of water soluble hydroxypropyl methylcellulose or polyethylene glycol. The inner-core may contain a binder such as paraffin, gelatin and dextrose, and the outer-layer may contain additives such as enzymes, buffering agents, sugars and manganese dioxide as an oxidation catalyst. When the tablets are placed in an aqueous environment, layers of the tablets dissolve over time releasing components therein.

21 Claims, 1 Drawing Sheet

TIMED-RELEASE TABLETS FOR BIOLOGICAL DEGRADATION OF ORGANIC MATTER

BACKGROUND OF THE INVENTION

1. Field of the Invention

This invention relates to a novel non-toxic in situ method for the accelerated biological degradation of organic matter in the form of sewage sludge or petroleum hydrocarbons on the surface of aquatic objects submerged in bodies of saltwater, brackish, or freshwater. The invention includes novel non-toxic compositions and novel products that are particularly useful for practicing the novel methods.

2. Description of the Prior Art

The delicate balance of our planets fragile aquatic ecosystems is being disturbed at an alarming rate. Industrial, agricultural, and residential effluents enter our waterways polluting these systems with organic, metallic and inorganic compounds. Current methods of remediating aquatic sediments contaminated with organic pollutants such as sewage, oil, pesticides, herbicides and polychlorinated biphenols involve dredging up the sediment and treating it elsewhere then returning it to the removal site. These existing methods are both expensive and damaging to benthic ecosystems by killing organisms. The need for an inexpensive, in situ and noninvasive method to remediate such situations has lead to the development of this novel method and compositions.

The applicant is aware of prior art which makes the novel method possible. The particles of the sodium carbonate peroxyhydrate mentioned as a part of the novel composition are created in a commonly used practice by spraying the pure compound with a solution containing sodium sulfate in a device know as a fluid bed dryer. The mixture then is heated to evaporate the solvent from solution. The size of the resulting particles is controlled by the length of time the resulting reaction is allowed to proceed before it is arrested by the drying process, the longer the reaction the larger the resulting particle size will become.

The aerobic bacteria, yeast and facultative anaerobic bacteria used in this method are placed into a dehydrated form by a commonly used method of thermal drying in which the incubator raised strain of bacteria are placed in a device which quickly evaporates the moisture from the culture without killing the bacteria or yeast. The resulting organisms are in a suspended state and will become active upon rehydration.

The enzymes used in the formulation of the novel composition are in dry crystallized form and can be chosen from the entire range of available enzymes. The enzyme(s) chosen will be particularly suited to help breakdown the contaminant being remediated, an example being protein kinases to breakdown proteins. Lyophilized enzymes are preferred.

The applicant is further aware of the following U.S. and Foreign Patents listed below and whose contents are herein incorporated by reference. U.S. Pat. No. 1,057,281 teaches the use of all peroxy compounds in an oxygen bath for medicinal purposes with people. U.S. Pat. No. 1,917,489 discloses the use of a solvent such as trichloroethylene, sodium peroxide and potassium carbonate in a system used to remove deposits from the inside walls of automotive radiators. U.S. Pat. No. 3,441,388 describes the use of sodium perborate and salts of peroxyacids and their use as oxygen generating agents to decrease the dissolving time of solid materials in water (i.e. laundry detergents). U.S. Pat. No. 3,502,429 features the use of sodium peroxide and potassium superoxide in a system which removes excess carbon dioxide from the atmosphere of a closed room, and replenished the oxygen taken up by respiration. U.S. Pat. No. 4,248,642 relates to the use of microsites of effervescence of a hypochlorite-peroxide interaction to loosen micro-deposits of debris and organic matter from reaction cells in an automated analytical instrument. U.S. Pat. No. 4,293,426 discloses the use of calcium peroxide particles coated with an insoluble organic compound, having a melting point of at least 50° C., used for water oxygenation. See in particular Col. 5, lines 45-58. U.S. Pat. No. 4,395,344 describes the use of percarbonate to mix the caustic substances with the water above the clog, in a dry drain opener preparation. U.S. Pat. No. 4,156,039 teaches the use of sodium percarbonate particles coated with sodium perborate and their use as oxygen generating agents in water. U.S. Pat. No. 4,025,453 relates to the activation of peroxide-based dry laundry bleaches in an aqueous medium with pH above 7.5 through the use of cyanamide. U.S. Pat. No. 4,026,798 describes the use of peroxygen compounds in a process for treatment of dirty dry cleaning bath solutions. U.S. Pat. No. 4,073,888 relates to the use of peroxy compounds as stabilizers for use with chlorine dioxide and quaternary ammonium salts as sterilizing agents. U.S. Pat. No. 4,086,175 discloses the activation of peroxide-based dry laundry bleaches in a buffered aqueous medium through the use of cyanamide and magnesium. U.S. Pat. No. 4,120,650 features the use of dry peroxygen compounds in conjunction with chlorine releasing compounds in a laundry detergent composition. U.S. Pat. NO. 4,197,198 teaches the use of peroxygen compounds as stabilizing agents for use with chlorine dioxide to degrade phenol compounds in a waste water stream. U.S. Pat. No. 4,251,486 features the use of sodium carbonate in a waste water treatment process for decomposing injurious substances. U.S. Pat. No. 4,253,971 teaches the use of peroxygen compounds as secondary algicide in the process of water treatment through the use of a linear polymeric biguanide. JP Patent 49-27799 relates to the use of calcium peroxide in fish culture to oxygenate breeding ponds. JP Patent 88-156001 discloses the use of oxygen generating compounds packed in gas-permeable nonwoven cloth bags for use in live fish transportation. JP Patent 89-51302 teaches the use of oxygen generating compounds packed in gas-permeable nonwoven polyethylene-coated cloth bags for use in live fish transportation.

SUMMARY OF THE INVENTION

This invention combats several aspects of the pollution problem in the environment. All involve treating the contamination at the site without disturbing the sediment and the animals and plants living there.

The first aspect of the invention is the accelerated degradation of organic matter on the submerged sediment surfaces. In the environment there is an enormous problem with the accidental or intentional introduction of organic matter in the form of raw or partially treated sewage into waterways. Pipe damage, rain water overflow, and out dated or overburdened sewage treatment facilities are the causes. The sewage sludge places a tremendous demand on the available dissolved oxygen levels resulting in a hazardous situation of low oxygen known as hypoxia. A typical hypoxic situation has dissolved oxygen levels of 2.0 milligrams per liter or less. This creates an environment which is toxic to many fish and aquatic invertebrates. As these fish and invertebrates die and fall to the bottom their decomposition adds to the oxygen depletion of the surrounding water. In the past the only way to remediate such mishaps would be to dredge up the contaminated sediment, treat it, and return it to the environment. This process is both expensive and potentially damaging to the organisms which are crucial to the balance of the sediments ecosystem. The most common alternative chosen is to do nothing which would be viable if the spills were not chronic and frequent. If left alone naturally occurring anaerobic bacteria would breakdown these compounds over a long period of time. However the huge quantity and frequency of these spills overburdens the sediment's ecosystem leading to oxygen deprivation and the death of many organisms necessary to the proper balance of the ecosystem. This type of damage can destroy ecosystems necessary to the propagation of commercially important species of fish and invertebrates. This invention proposes an in situ approach to help remediate this problem. Its approach is one in which the ability of naturally occurring and/or seeded microorganisms to breakdown these contaminants is enhanced by the timed-release of oxygen gas, via chemical reaction, and chemical additives such as buffering agents and enzymes. This method proposes that situations, where aerobic bacteria no longer exist due to low oxygen levels, can be reseeded with timed-release tablets having an inner-core of dehydrated living bacteria. The choice of which additional additives to enhance the process, buffer the pH, and control the dissolving rate of the tablet, will depend upon each particular situation. As shown in FIG. 3, the rising bubbles of oxygen, #23, also act to mechanically loosen and resuspend the particles of organic matter, #21, around the tablet, allowing for greater exposed surface area of the particle accessible to bacteria and other microorganisms which can break it down at an accelerated pace. The catabolic processes which could normally take months now occur in hours or days due to the accelerated growth of the aerobic organisms. Once the organic matter is completely broken down, the bacterial food source is depleted. Then the bacteria start to die off, eventually returning their number to precontamination balanced levels.

The second aspect of the invention deals with the problem of pH balance in aquatic systems. At present acid-contaminated lakes and streams have been remediated by the introduction of large quantities of alkali such as lime $Ca(OH)_2$ in a process known as liming. Liming produces a sharp rise in pH, causing a shock to the ecosystem resulting in the death of algae and invertebrates. These dead organisms fall to the bottom adding to the layer of decomposing organic matter created by the death of organisms already killed by the acid contamination itself. This layer decaying organic matter puts an increased demand on the available oxygen levels in the water above the sediment. This bottom water quickly becomes hypoxic, thereby causing the death of additional animals and plants, starting a cycle of death. Eventually, over a period of time the lake will recover after liming to its proper pH level. This is the goal of liming, but it is short lived because of the chronic input of acid rain. The lake will have to be retreated periodically.

The death cycle can be broken, however, by the use of the novel composition, which will act to buffer and stabilize the pH in a slow, time-release manner rather than a sharp rise as in traditional liming methods. The novel composition also simultaneously raises available oxygen levels preventing hypoxia, and seeds aerobic bacterial growth in anaerobic sediments which are overburdened with decaying organic matter.

In some freshwater lakes, the problem of pH balance is different then that found in saltwater lakes, because of a lack of buffering compounds in the water matrix and surrounding soils and sediment. This reduced buffering capacity of the lake water results in wide fluctuations of pH after acid rain events. These fluctuations can prove to be deadly to aquatic organisms. The optimum pH level is in the 6.8 to 7.8 range depending upon the type of fish and invertebrates found in the lake. This situation requires the addition of a weak acid to the novel composition to achieve the proper pH in the final solution and a buffering agent to stabilize it. Other buffering agents which serve to control pH can be used. They include acetates such as calcium magnesium acetate, borates, and phosphate buffering agents.

A third aspect of the invention deals with the oxygenation and seeding of hypoxic bottom waters, referred to as hypolimnion, with aerobic and/or anaerobic bacterial cysts and/or yeast cysts. During prolonged, warm, calm weather, a thermocline usually develops separating cold, dense bottom water from the warm surface layer and from atmospheric oxygen. Bacterial degradation of organic matter on the seabed is likely to reduce oxygen levels in bottom water or hypolimnion under these circumstances. There is also a difference in dissolved oxygen saturation points between fresh and saltwater. In freshwater the saturation level of dissolved oxygen at 77° F. is approximately 5.9 milligrams per liter. This is much higher than that of saltwater at the same temperature. Because of this there can be a greater potential for hypoxia, low oxygen levels, in marine bottom water overburdened with decaying organic matter. Dangerously low oxygen concentrations can result thereby damaging the ecosystem and the environment. Low levels of oxygen in bottom waters can be raised by dispersing on to or below the surface of the water, above the zone in question, a quantity of timed-release tablets such as those shown in FIG. 1, of a dry particulate composition consisting essentially of an outer-coating of a water soluble substance such as hydroxypropyl methylcellulose or polyethylene glycol #1 and #9, over an outer-layer of an oxidative alkali such as sodium sulfate coated sodium carbonate peroxyhydrate particles, additives including enzymes such as protein kinases, buffering agents such as magnesium carbonate, acetates, borates, and phosphates and acids such as citric or sulfamic acid, sugars such as dextrose, oxidation catalysts such as manganese dioxide #3 and #11, an inner-coating of a water soluble substance such as hydroxypropyl methylcellulose or polyethylene glycol #5 and #13 and an inner-core of dehydrated aerobic or facultative anaerobic and yeast bacterial cysts in a paraffin or gelatin binder and dextrose #7 and #15.

A fourth aspect of this invention deals with treating aquarium gravel or aquaculture pond sediment, which is contaminated with an overload of decaying organic matter. This situation can be remediated using an approach similar to the one mentioned above. This approach is one in which the ability of naturally occurring and/or seeded aerobic microorganisms ability to breakdown these contaminants is enhanced by the timed-release of oxygen gas, via chemical reaction, and chemical additives such as buffering agents and enzymes. The choice of which additional additives to enhance the process, buffer the pH, and control the dissolving rate of the tablet, will depend upon each particular situation. The rising bubbles of oxygen also act to mechanically loosen and resuspend the particles of organic matter around the tablet, allowing for greater exposed surface area of the particle accessible to bacteria and other microorganisms which can break it down at an accelerated pace.

An object of the present invention is to provide an novel non-toxic in situ method for the accelerated biological degradation of organic matter in the form of sewage sludge on the surface of aquatic sediments in water by dispersing on to or below the surface of the water a quantity of timed-release tablets. Said tablets sink, then dissolve in layers, releasing oxygen bubbles which mechanically loosen and resuspend the organic matter increasing the surface area available to bacteria. When the inner-core of the tablets dissolve aerobic bacteria are released. The bacteria then feed on the sewage sludge at an accelerated pace.

An additional object of this invention is to provide novel nontoxic in situ method for the accelerated biological degradation of organic matter in the form of petroleum hydrocarbons on the, surface of aquatic sediments in water by dispersing on to or below the surface of the water a quantity of timed-release tablets. Said tablets sink, then dissolve in layers, releasing oxygen bubbles which mechanically loosen and resuspend the organic matter increasing the surface area available to bacteria. When the inner-core of the tablets dissolve aerobic bacteria are released. The bacteria then feed on the petroleum hydrocarbons at an accelerated pace.

Another object of this invention is to provide novel nontoxic compositions and novel products that are particularly useful in practicing the novel methods.

A further object of this invention is to provide novel nontoxic in situ methods to oxygenate and seed with aerobic bacteria the hypoxic bottom waters of lakes, streams, bays, and estuaries in a timed-release manner by dispersing on to or below the surface of the water a quantity of timed-release tablets. Said tablets sink then dissolve in layers, releasing oxygen bubbles which raise the dissolved oxygen in a controlled manner and reseed aerobic bacterial populations.

Still a further object of this invention is to provide a device #17 which is used to dispense the tablets of the novel composition on the surface of the body of water from the side or rear of a boat.

Another object of this invention is to provide a device #19 which is used to dispense the tablets of the novel composition below the surface of the body of water from the side or rear of a boat.

Still a further object of this invention is to treat acid-contaminated lakes and streams by buffering the pH and raising dissolved oxygen levels and seeding aerobic bacteria via the timed-release tablets of the novel composition.

Another object of this invention is to provide novel compositions and novel products containing chemical ingredients for aiding in achieving the proper pH and dissolved oxygen and aerobic bacterial levels of surface and bottom water and sediment in acid-contaminated lakes and streams.

DESCRIPTION OF THE PREFERRED EMBODIMENTS

Sodium carbonate peroxyhydrate particles coated with sodium sulfate, are dry solids at room temperatures, are nontoxic to humans and to aquatic life, and react with water to release oxygen in such form that matter is loosened and removed from surfaces in the water, but does not remove the protective mucous coatings on fish that are in the water. The size of the particles chosen for use in the tablets is decided according to the rate of oxygen release that is desired. In addition, binding agents such as polyethylene glycol and coating agents such as methylcell can be added to achieve a time-released, tabletized version of the novel composition.

Various dry-powder additives can be included in the novel composition, which do not interfere with the cleaning action of the oxidant, but provide beneficial effects in the aquatic environment. For example, magnesium carbonate may be included because it helps to maintain the proper balance of magnesium-to-calcium in the saltwater, so that magnesium is not leached from sensitive invertebrates such as anemones. Citric acid can be included in the novel composition to adjust the pH of the water in a safe range. Other buffering agents which serve to control pH can be used. They include acetates such as calcium magnesium acetate, borates, and phosphate buffering agents.

The tablets themselves can be created by several methods including the following example. The following is only one example and is not intended to limit the scope of the invention to the preferred embodiments mentioned. This example involves the use of several steps. In the first step is the creation of the inner core of the tablet. This is accomplished by dry mixing the heat-dried bacterial cysts with binding agents such as a paraffin or a gelatine, and/or a sugar such as dextrose. Any strain of aerobic or facultative anaerobic bacteria or yeast that is capable of forming cysts, endospores or ascospores in adverse conditions can be used. The strain or strains chosen will depend upon their availability to breakdown the contaminant being remediated as well as their ability to survive in the particular aqueous environment. These strains include the bacterial genera Bacillus, Sporolactobacillus, Sporosarcina, Sphaerotilus, Beggiatoa, and Micrococcus. Also any yeast may be included, such as those within the genera Saccharomyces.

The formulation of the protective coat, cyst, endospore, and ascospore enable the bacteria or yeast to survive long periods of time without food or moisture. When placed in a hydrated environment, the organism breaks out of its protective coating and grows and reproduces. These types of organisms can be artificially induced to form cysts, endospores or ascospores by a commonly used method of dehydration known as heat drying. A common example of a product created by this method is the dry powdered yeast used in baking and brewing.

This mixture is then pressed into small tablets of approximately 50 milligrams by the use of any known compactor such as a roller-type or rotary pelletizer. The small tablets can then be coated with a water soluble substance, such as hydroxypropyl methylcellulose, in a device such as a drum dryer. In this process the tablets are sprayed while moving with a liquid solution containing the coating material. The solvent is then heat evaporated in the dryer. The second step involves compressing the core tablet within the center of the larger final tablet. This is accomplished by a device known as rotary double tabletizer such as the Korsch Pharmakontroll 2.03. This device allows for the core tablet to be positioned in the center while the outer-layer of approximately 600 milligrams of the oxidative alkali/additive mixture is compressed around it. The third and final step involve coating the final tablet with a water soluble coating such as hydroxypropyl methylcellulose in a drum dryer. In this process the tablets are sprayed while moving with a liquid solution containing the coating material. The solvent is then heat evaporated in the dryer.

The preferred embodiment of the instant invention is timed-release tablets of a dry particulate composition consisting essentially of an inner-core of dehydrated bacterial cysts, an inner-coating of a water soluble substance such as hydroxypropyl methylcellulose, an outer-layer of an oxidative alkali such as sodium sulfate coated sodium carbonate peroxyhydrate particles, and an outer-coating of a water soluble substance such as hydroxypropyl methylcellulose.

The timed-release tablets according to the instant invention may contain 10% to 95% by weight of the inner-core additives such as a parraffin or a gelatin bind, and/or sugars such as dextrose.

The timed-release tablets according to the instant invention may also contain from 0.1% to 20% by weight of the outer layer additives including enzymes such as protein kinases, buffering agents such as magnesium carbonate, acetates, borates and phosphates and acids such as citric or sulfamic acid, sugars such as dextrose, and oxidation catalysts such as manganese dioxide.

The outer-coating timed-release tablets according to the instant invention is a water soluble compound comprising from 0.1% to 5% by weight of the entire tablet.

The inner-core coating of the timed-release tablets according to the instant invention is from 0.1% to 5% by weight of the inner-core.

Figure 1:
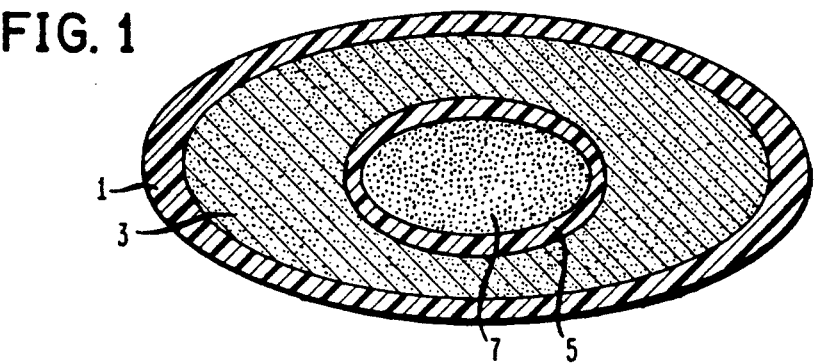
FIG. 1 is a cross-sectional view of a timed-release tablet with a single inner-core with #1 being the outer-coating, #3 being the oxidative compound mixture, #5 being the inner-core coating, and #7 being the bacterial core.
Figure 2:
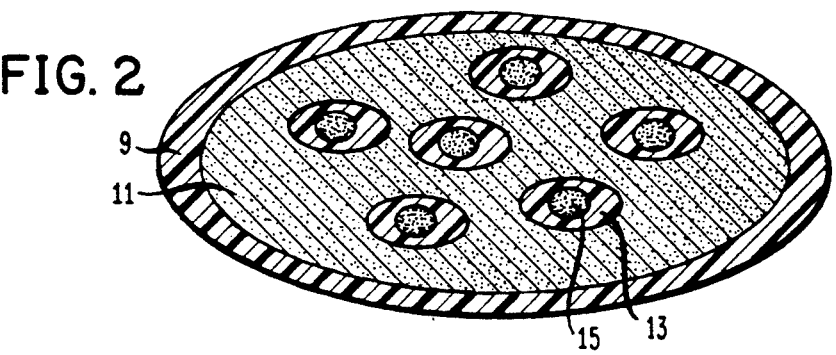
FIG. 2 is an cross-sectional view of a timed-release tablet with multiple inner-cores with #9 being the outer-coating, #11 being the oxidative compound mixture, #13 being an inner-core coating, and #15 being one of several bacterial cores.
Figure 3:
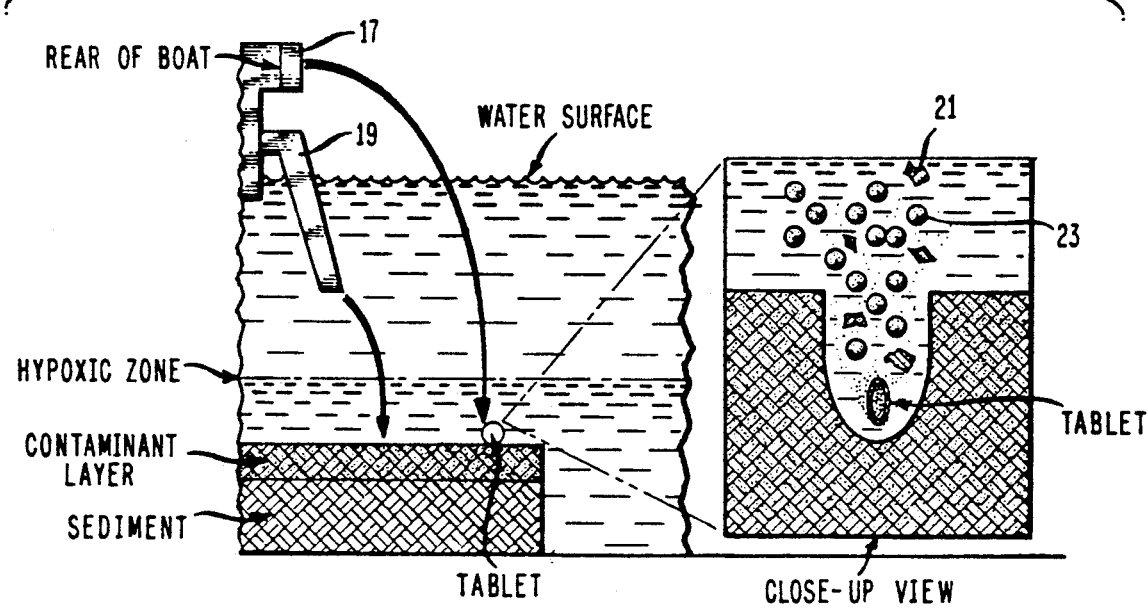
FIG. 3 is an elevational view of a body of water wherein organic matter is being degraded from surface of the sediment through the use of the novel composition. #17 is a device that dispenses tablets off the back of a boat on to the surface of the water in a controlled manner. #19 is a device that dispenses tablets off the back of a boat below the surface of the water in a controlled manner. #21 is a particle of contamination which has been loosened form the contamination layer and is suspended in the water above the sediment. #23 is a rising bubble of oxygen which has been generated from the dissolving tablet.

The following description of some of the preferred embodiments of the concepts of this invention is made in reference to the accompanying figures.

The following example serves to provide a better understanding of the invention, without however limiting the scope of the invention to the embodiments described.

EXAMPLE 1

The following are the key steps required to carry out an environmental clean-up operation:

First the design of the initial sampling and testing program is customized to fit the situation and will include four general areas:

1. Sampling Grid Pattern—is the actual location of the sample sites and is dependent upon the size shape and depth of the location as well as proximity to possible sources or inputs of pollutants.

2. Diurnal Study—is the sampling of the chosen number of sampling points over a period of 24 hours. The test parameters include temperature, pH, dissolved oxygen, specific conductivity, tidal flux, and weather conditions.

3. Depth Profile—this type of sampling involves the taking of samples at different depths and includes parameters such as biochemical oxygen demand (BOD), chemical oxygen demand (COD), total organic carbon (TOC), ammonia, nitrate, nitrite, total Kjeldahl nitrogen (TKN), hydrogen sulfide ($H_2S$), total phosphate (T-PO4), ortho-phosphate (O-PO4), specific conductivity, temperature, total dissolved solids (TDS), total suspended solids (TSS), turbidity and chlorophyll A.

4. Sediment Analysis—the biological portion of this type involves the identification of benthic organisms macroinvertebrates and bacteria, as well as chemical analysis including parameters as Total Organic Carbon (TOC), redox potential, total metals (As, Cd, Cr, Pb, Hg, Zn, Cu, Fe).

The initial testing will be carried out EPA guidelines and safe laboratory practices. Sample will be taken using EPA guidelines and in' properly preserved containers. A chain-of-custody will be maintained throughout the analysis. Water samples will be collected using non-contaminating hand dippers at the surface or Nanson or Niskin sampling devices at the surface depth. Sediment samples will obtained using a hand corer if the water is shallow and a Ekman or ponar grab sampler if the water is deep.

Results of the analysis are then plotted graphically in order to determine a baseline and to see any indication of either over acidification due to acid precipitation or oxygen demand overload due organic pollution such as sewage. If it is found that the treatment will reduce the BOD and or COD and breakdown the organic matter with out producing toxic residuals such as the oxidized form of mercury, than the project will move to the next phase if not alternatives will be discussed with the client.

The decision to proceed will depend on what effects adding oxygen gas would in compensating for the demand or in the acid situation what the buffering capacity of the product may due to the pH. If any of the heavy metals are found in high concentration in solution and the solution is in the acid range (below 7.0) than the treatment would be beneficial in precipitating the metals out of solution. It might be advisable to add additional compounds (specific to the metal) to actively chelate the metal into a complex which is biologically inactive. If the Biochemical Oxygen Demand (BOD) and Chemical Oxygen Demand (COD) in the contaminated zone are 50% higher than that of a non-contaminated site in the area and the Dissolved Oxygen (DO) level is below 2.0 milligrams per liter, then the site is good candidate for treatment.

The custom design of the treatment will depend on the type and extent of pollution and the chemistry of the water. If for example, the problem is acid rain contamination, then the product must be buffered to achieve the proper pH. If the pH of the water is lower than 6.3 than this particular method would not be recommended especially is high metal concentrations such as mercury, are found because the oxidation of metallic complexes can cause them to become even more toxic.

If the problem is untreated sewage sludge which has accumulated on the sediment surface then the product should be pressed into tablets. There size and shape will depend upon the conditions of the site and include; depth of contaminant sludge depth to the sediment surface, current strength and direction, water surface conditions, and weather. In order to predict where a tablet will land on the bottom once dropped from the surface. To determine this the currents at the site must be studied. The faster the current, the quicker the tablet will need to sink. This is accomplished by pressing smaller rounder tablets. An example would be 500 milligram spherical tablets. In slow, calm water flat disk-like or elongated tablets can be used.

The actual treatment can take three forms. The first will involve spreading the granular product over the surface of the contaminated area. This will be accomplished using a boat with a hopper/spreader device #17 installed over the stern. The device has a hopper which is loaded with granular product or tablets and as the boat moves along its course the spreader shoots the product into the water. The rate at which the product is added to the water can be controlled by the amount of product being released from the hopper to the spreader and on the speed at which the boat travels. The course or pattern which the boat takes will depend upon the site conditions and the type and location of the contamination. If the water column is being treated, as is the case when granular product is required, a high boat speed and loose pattern can be used.

The second situation involves spreading tabletized product into the water using the same device #17 if the contamination is concentrated in the sediment. In that case tablets should be applied at a slow speed and tight overlapping pattern is required.

The third situation involves spreading tabletized product into the water using the device #19 if the contamination is concentrated in the sediment. This device is used when the contamination is concentrated in small specific area. It enables the crew to place tablet on to a specific spot on the sediment surface with great accuracy.

Testing should be continue during the treatment process. This is done to see if the treatment is having a beneficial effect and to see if any adjustments need to be made. The parameters at least include dissolved oxygen, BOD, COD, pH, temperature, conductivity, TSS, TDS, Turbidity, and total metals. If dissolved metal concentrations are rising then the process should be stopped and reevaluated. A temporary rise in BOD, COD, TSS, and Turbidity should be followed by a drop and leveling off at a value which is within the acceptable range for the specific situation. If the pH is raising to quickly the process should be stopped and the concentrations being added should be reduced accordingly.

Follow-up testing should be continued until a steady baseline is achieved. It should be noted that there are daily and seasonal variations which must be accounted in the evaluation of the steady baseline and the decision to terminate the testing. The parameters should include as many of the ones listed above.

The foregoing figures and descriptions thereof are provided as illustrative of some of the preferred embodiments of the concepts of this invention. While these embodiments represent what is regarded as the best modes for practicing this invention, they are not intended as delineating the scope of the invention, which is set forth in the following claims. It will be understood that the above descriptions of the present invention are susceptible to various changes, modifications and adaptations, and the same are intended to be comprehended within the meaning and range of equivalents of the appended claims.

What is claimed is:

1. Timed-release tablets of a dry particulate composition consisting essentially of an inner-core of dehydrated bacterial cysts, and inner-coating over said inner-core of water soluble hydroxypropyl methylcellulose, an outer-layer over said inner-coating of sodium sulfate coated sodium carbonate peroxyhydrate particles, and an outer-coating over said outer-layer of water soluble hydroxypropyl methylcellulose.

2. The timed-release tablets according to claim 1 in which the inner-core further consist essentially of 10% to 95% by weight of a binder selected from the group consisting of paraffin, gelatin binder, dextrose and combinations thereof.

3. The timed-release tablets according to claim 1 in which the outer-layer further consist essentially of from 0.1% to 20% by weight additives selected from the group consisting of enzymes; buffering agents selected from the group consisting of magnesium carbonate acetates, borates, phosphates, citric acid and sulfamic acid manganese dioxide as an oxidation catalyst; and combinations thereof.

4. The timed-release tablets according to claim 1, in which the outer-coating is from 0.1% to 5% by weight of the entire tablet.

5. The timed-release tablets according to claim 1, in which the inner-coating over said inner-core is from 0.1% to 5% by weight of the inner-core.

6. The timed-release tablets according to claim 1 in which the bacterial cysts are aerobic.

7. The timed-release tablets according to claim 1 in which the bacterial cysts are facultative anaerobic.

8. The timed-release tablets according to claim 1 in which the bacterial cysts are yeast.

9. The timed-release tablets according to claim 1 which have more than one inner-core.

10. The timed-release tablets according to claim 9 in which the more than one inner core further consists essentially of 10% to 95% by weight binder selected from the group consisting of paraffin, gelatin, dextrose, and combinations thereof.

11. The timed-release tablets according to claim 9 in which the outer layer further consists essentially of from 0.1% to 20% by weight additives selected from the group consisting of protein kinases; buffering agents selected from the group consisting of magnesium carbonate, acetates, borates, phosphates, citric acid and sulfamic acid; manganese dioxide as an oxidation catalyst; and combination thereof.

12. The timed-release tablets according to claim 9, in which the outer coating is from 0.1% to 5% by weight of the entire tablet.

13. The timed-release tablets according to claim 9 in which the inner-cores coating comprises from 0.1% to 5% by weight of the inner-cores.

14. Timed-release tablets of a dry particulate composition comprising
  (1) an inner-core comprising at least one live microorganism strain in dormant condition selected from the group consisting of aerobic bacteria, facultative anaerobic bacteria and yeast which are capable of forming cysts, endospores or ascospores in adverse conditions,
  (2) an inner-coating over the inner-core of a water soluble substance selected from the group consisting of hydroxypropyl methylcellulose and polyethylene glycol.
  (3) an outer-layer over said inner-coating comprising sodium sulfate coated sodium carbonate peroxyhydrate particles, and
  (4) an outer-coating over the outer-layer of a water soluble substance selected from the group consisting of hydroxypropyl methylcellulose and polyethylene glycol.

15. The timed-release tablets of claim 14 wherein the inner-core further contains a binder selected from the group consisting of paraffin, gelatin and dextrose.

16. The timed-release tablets of claim 14 wherein the outer layer further contains at least one additive selected from the group consisting of enzymes, buffering agents, sugars and oxidation catalysts.

17. The timed-release tablets of claim 16 wherein the additives are selected from the group consisting of protein kinase enzymes; buffering agents selected from the group of magnesium carbonate, acetates, borates, phosphates, citric acid and sulfamic acid; dextrose and manganese dioxide as an oxidation catalyst.

18. The timed-release tablets of claim 14 wherein the live microorganism strain is selected from the group consisting of genera Bacillus, Sporolactobacillus, Sporosarcina, Sphaerotilus, Beggiatoa, Micrococcus and yeast within the genera saccharomyces.

19. The timed-release tablets of claim 15 wherein the binder comprises 10 to 95% by weight of the inner-core.

20. The timed-release tablets of claim 16 wherein the additives comprise 0.1 to 20% by weight of the outer-layer.

21. The timed-release tablets of claim 14 wherein the outer-coating comprises from 0.1 to 5% by weight of the entire tablet.

* * * * *